US010039664B2

(12) United States Patent
Grim et al.

(10) Patent No.: US 10,039,664 B2
(45) Date of Patent: Aug. 7, 2018

(54) OVERMOLDING FOR AN ORTHOPEDIC WALKING BOOT

(71) Applicant: OVATION MEDICAL, Agoura Hills, CA (US)

(72) Inventors: Tracy E. Grim, Thousand Oaks, CA (US); Steven L. Hecker, Los Angeles, CA (US); Kenji Watabe, Ventura, CA (US); Ryan C. Cohn, Torrance, CA (US); Tim Crowley, Ventura, CA (US); Veneza Yuzon, Calabasas, CA (US)

(73) Assignee: ORTHO SYSTEMS, Agoura Hills, CA (US)

( * ) Notice: Subject to any disclaimer, the term of this patent is extended or adjusted under 35 U.S.C. 154(b) by 970 days.

(21) Appl. No.: 14/214,319

(22) Filed: Mar. 14, 2014

(65) Prior Publication Data
US 2014/0265018 A1 Sep. 18, 2014

Related U.S. Application Data

(60) Provisional application No. 61/801,843, filed on Mar. 15, 2013, provisional application No. 61/916,077, filed on Dec. 13, 2013.

(51) Int. Cl.
B29C 45/14 (2006.01)
A61F 5/01 (2006.01)

(52) U.S. Cl.
CPC .......... A61F 5/0195 (2013.01); A61F 5/0111 (2013.01); B29C 45/14008 (2013.01); B29C 45/14467 (2013.01); B29C 2045/1454 (2013.01)

(58) Field of Classification Search
None
See application file for complete search history.

(56) References Cited

U.S. PATENT DOCUMENTS

| 143,537 | A | | 10/1873 | Silberschmidt | |
|---|---|---|---|---|---|
| 1,472,415 | A | | 10/1923 | Haggerty | |
| 2,643,468 | A | | 6/1953 | Gottschalk | |
| 2,959,169 | A | | 11/1960 | Bless | |
| 3,175,249 | A | * | 3/1965 | Ferreira | B29D 35/061 264/244 |
| 3,178,496 | A | * | 4/1965 | Ferreira | B29D 35/061 249/82 |
| 3,246,068 | A | * | 4/1966 | Ferreira | B29D 35/061 264/244 |

(Continued)

FOREIGN PATENT DOCUMENTS

CN 201085714 Y 7/2008
CN 201523712 U 7/2010

(Continued)

OTHER PUBLICATIONS

PCT Publication No. WO/87/03471, dated Jun. 18, 1987, regarding PCT Application No. PCT/US86/02670.

(Continued)

Primary Examiner — Edmund H Lee
(74) Attorney, Agent, or Firm — Fulwider Patton LLP

(57) ABSTRACT

A method of manufacturing an orthopedic walking boot, comprising providing a base configured to support a user's foot and receive a support assembly configured to support the user's lower leg; and overmolding an outer sole to the base.

22 Claims, 8 Drawing Sheets

(56) References Cited

U.S. PATENT DOCUMENTS

| | | |
|---|---|---|
| 3,284,558 A * | 11/1966 | Ludwig ............... A43B 1/0027 |
| | | 264/244 |
| 3,400,429 A * | 9/1968 | Ludwig ............... A43B 1/0027 |
| | | 264/244 |
| 3,441,643 A * | 4/1969 | Janssen ............... B29D 35/062 |
| | | 264/244 |
| 3,464,126 A | 9/1969 | Sarkissian |
| 3,504,668 A | 4/1970 | Boudon |
| 3,661,151 A | 5/1972 | Schoenbrun et al. |
| 3,665,619 A | 5/1972 | Gray |
| 3,792,537 A | 2/1974 | Plank et al. |
| 3,805,773 A | 4/1974 | Sichau |
| 3,814,088 A | 6/1974 | Raymond |
| 3,955,565 A | 5/1976 | Johnson |
| 3,976,059 A | 8/1976 | Lonardo |
| 4,005,704 A | 2/1977 | Stöhr et al. |
| 4,053,995 A | 10/1977 | Shein |
| 4,057,056 A | 11/1977 | Payton |
| 4,094,312 A | 6/1978 | Whyte |
| 4,100,686 A | 7/1978 | Sgarlato et al. |
| 4,100,918 A | 7/1978 | Glancy |
| 4,184,273 A | 1/1980 | Boyer et al. |
| 4,188,735 A | 2/1980 | Hahn |
| 4,215,491 A | 8/1980 | Giannetti |
| 4,217,706 A | 8/1980 | Vartanian |
| 4,265,033 A | 5/1981 | Pois |
| 4,268,931 A | 5/1981 | Salomon |
| 4,393,866 A | 7/1983 | Finnieston |
| 4,446,856 A | 5/1984 | Jordan |
| 4,454,871 A | 6/1984 | Mann et al. |
| 4,494,536 A | 1/1985 | Latenser |
| 4,497,070 A | 2/1985 | Cho |
| 4,505,269 A | 3/1985 | Davies et al. |
| 4,510,927 A | 4/1985 | Peters |
| 4,550,721 A | 11/1985 | Michel |
| 4,556,054 A | 12/1985 | Paulseth |
| 4,559,934 A | 12/1985 | Philipp |
| 4,567,678 A | 2/1986 | Morgan et al. |
| 4,572,169 A | 2/1986 | Mauldin et al. |
| 4,587,962 A | 5/1986 | Greene et al. |
| 4,590,932 A | 5/1986 | Wilkerson |
| 4,624,247 A | 11/1986 | Ford |
| 4,628,945 A | 12/1986 | Johnson, Jr. |
| 4,665,904 A | 5/1987 | Lerman |
| 4,771,768 A | 9/1988 | Crispin |
| 4,805,601 A | 2/1989 | Eischen, Sr. |
| 4,825,856 A | 5/1989 | Nelson |
| 4,844,094 A | 7/1989 | Grim |
| 4,862,900 A | 9/1989 | Hefele |
| 4,872,273 A | 10/1989 | Smeed |
| 4,879,822 A | 11/1989 | Hayes |
| 4,919,118 A | 4/1990 | Morris |
| 4,941,271 A | 7/1990 | Lakic |
| 4,947,838 A | 8/1990 | Giannetti |
| 4,964,402 A | 10/1990 | Grim et al. |
| 4,974,583 A | 12/1990 | Freitas |
| 4,982,733 A | 1/1991 | Broadhurst et al. |
| 4,999,932 A | 3/1991 | Grim |
| 5,020,523 A | 6/1991 | Bodine |
| 5,078,128 A | 1/1992 | Grim et al. |
| 5,086,761 A | 2/1992 | Ingram |
| 5,088,478 A | 2/1992 | Grim |
| 5,088,479 A | 2/1992 | Detoro |
| 5,088,481 A | 2/1992 | Darby |
| 5,092,321 A | 3/1992 | Spademan |
| 5,125,400 A | 6/1992 | Johnson, Jr. |
| 5,154,695 A | 10/1992 | Farris et al. |
| 5,176,623 A | 1/1993 | Stetman et al. |
| 5,197,942 A | 3/1993 | Brady |
| 5,213,564 A | 5/1993 | Johnson, Jr. et al. |
| 5,219,324 A | 6/1993 | Hall |
| 5,226,245 A | 7/1993 | Lamont |
| 5,226,875 A | 7/1993 | Johnson |
| 5,233,767 A | 8/1993 | Kramer |
| 5,242,379 A | 9/1993 | Harris et al. |
| 5,277,695 A | 1/1994 | Johnson, Jr. et al. |
| RE34,661 E | 7/1994 | Grim |
| 5,329,705 A | 7/1994 | Grim et al. |
| 5,330,419 A | 7/1994 | Toronto |
| 5,334,135 A | 8/1994 | Grim et al. |
| 5,352,189 A | 10/1994 | Schumann et al. |
| 5,353,525 A | 10/1994 | Grim |
| 5,367,789 A | 11/1994 | Lamont |
| 5,368,551 A | 11/1994 | Zuckerman |
| 5,370,133 A | 12/1994 | Darby et al. |
| 5,370,604 A | 12/1994 | Bernardoni |
| 5,378,223 A | 1/1995 | Grim et al. |
| 5,383,290 A | 1/1995 | Grim |
| 5,384,970 A | 1/1995 | Melton |
| 5,392,534 A | 2/1995 | Grim |
| 5,399,152 A | 3/1995 | Habermeyer et al. |
| 5,399,155 A | 3/1995 | Strassburg et al. |
| 5,407,421 A | 4/1995 | Goldsmith |
| 5,425,701 A | 6/1995 | Oster et al. |
| 5,426,872 A | 6/1995 | Hayes |
| 5,429,588 A | 7/1995 | Young et al. |
| 5,441,015 A | 8/1995 | Farley |
| 5,445,602 A | 8/1995 | Grim et al. |
| 5,460,599 A | 10/1995 | Davis et al. |
| 5,464,385 A | 11/1995 | Grim |
| 5,483,757 A | 1/1996 | Frykberg |
| 5,496,263 A | 3/1996 | Fuller, II et al. |
| 5,503,622 A | 4/1996 | Wehr |
| 5,507,720 A | 4/1996 | Lampropoulos |
| 5,526,586 A | 6/1996 | Foscaro |
| 5,527,269 A | 6/1996 | Reithofer |
| 5,551,950 A | 9/1996 | Oppen |
| 5,554,104 A | 9/1996 | Grim |
| 5,571,077 A | 11/1996 | Klearman et al. |
| 5,577,998 A | 11/1996 | Johnson, Jr. et al. |
| 5,582,579 A | 12/1996 | Chism et al. |
| 5,609,570 A | 3/1997 | Lamont |
| 5,617,650 A | 4/1997 | Grim |
| 5,620,411 A | 4/1997 | Schumann et al. |
| 5,632,723 A | 5/1997 | Grim |
| 5,641,322 A | 6/1997 | Silver et al. |
| 5,675,839 A | 10/1997 | Gordon et al. |
| 5,761,834 A | 6/1998 | Grim et al. |
| 5,762,622 A | 6/1998 | Lamont |
| 5,772,619 A | 6/1998 | Corbett |
| 5,776,090 A | 7/1998 | Bergmann et al. |
| 5,799,659 A | 9/1998 | Stano |
| 5,823,981 A | 10/1998 | Grim et al. |
| 5,827,210 A | 10/1998 | Antar et al. |
| 5,827,211 A | 10/1998 | Sellinger |
| 5,833,639 A | 11/1998 | Nune et al. |
| 5,836,902 A | 11/1998 | Gray |
| 5,853,381 A | 12/1998 | Stevenson et al. |
| 5,857,987 A | 1/1999 | Habermeyer |
| 5,865,166 A | 2/1999 | Fitzpatrick et al. |
| 5,868,690 A | 2/1999 | Eischen, Sr. |
| 5,887,591 A | 3/1999 | Powell et al. |
| 5,891,073 A | 4/1999 | Deirmendjian et al. |
| 5,897,515 A | 4/1999 | Willner et al. |
| 5,897,520 A | 4/1999 | Gerig |
| 5,902,259 A | 5/1999 | Wilkerson |
| 5,913,841 A | 6/1999 | Lamont |
| 5,925,010 A | 7/1999 | Caprio, Jr. |
| 5,951,504 A * | 9/1999 | Iglesias ............... A61F 5/0111 |
| | | 602/16 |
| 5,954,075 A | 9/1999 | Gilmour |
| 5,961,477 A | 10/1999 | Turtzo |
| 5,980,475 A | 11/1999 | Gibbons |
| 5,993,404 A | 11/1999 | McNiel |
| 6,019,741 A | 2/2000 | Prieskorn |
| 6,021,780 A | 2/2000 | Darby |
| 6,024,712 A | 2/2000 | Iglesia et al. |
| 6,027,468 A | 2/2000 | Pick |
| 6,044,578 A | 4/2000 | Kelz |
| 6,056,712 A | 5/2000 | Grim |
| 6,126,625 A | 10/2000 | Lundberg |
| 6,154,983 A | 12/2000 | Austin |
| 6,155,998 A | 12/2000 | Gilmour |
| 6,189,172 B1 | 2/2001 | Baek |

(56) References Cited

U.S. PATENT DOCUMENTS

| | | |
|---|---|---|
| 6,228,044 B1 | 5/2001 | Jensen et al. |
| 6,247,250 B1 | 6/2001 | Hauser |
| 6,267,742 B1 | 7/2001 | Krivosha et al. |
| 6,277,087 B1 | 8/2001 | Hess et al. |
| 6,282,816 B1 | 9/2001 | Rosendahl |
| 6,282,818 B1 | 9/2001 | Lu |
| 6,334,854 B1 | 1/2002 | Davis |
| 6,350,246 B1 | 2/2002 | DeToro |
| 6,361,514 B1 | 3/2002 | Brown et al. |
| 6,361,515 B1 | 3/2002 | Gilmour |
| 6,374,516 B1 | 4/2002 | Bonaventure et al. |
| 6,406,450 B1 | 6/2002 | Kowalczyk et al. |
| 6,409,695 B1 | 6/2002 | Connelly |
| 6,432,073 B2 | 8/2002 | Prior et al. |
| 6,491,654 B2 | 12/2002 | Lamont |
| D473,654 S | 4/2003 | Iglesias et al. |
| 6,558,339 B1 | 5/2003 | Graham |
| 6,572,571 B2 | 6/2003 | Lowe |
| 6,648,843 B1 | 11/2003 | Marciano et al. |
| 6,656,145 B1 | 12/2003 | Morton |
| 6,682,497 B2 | 1/2004 | Jensen et al. |
| 6,699,209 B2 | 3/2004 | Turtzo |
| 6,722,060 B2 | 4/2004 | Okajima |
| 6,755,798 B2 | 6/2004 | McCarthy et al. |
| 6,796,058 B2 | 9/2004 | Potchatko |
| D500,855 S | 1/2005 | Pick et al. |
| 6,866,043 B1 | 3/2005 | Davis |
| 6,923,780 B2 | 8/2005 | Price et al. |
| 6,945,946 B2 | 9/2005 | Rooney |
| 6,945,947 B2 | 9/2005 | Ingimundarson et al. |
| 6,955,654 B2 | 10/2005 | Gilmour |
| 6,976,972 B2 | 12/2005 | Bradshaw |
| 6,979,287 B2 | 12/2005 | Elbaz et al. |
| 6,991,613 B2 | 1/2006 | Sensabaugh |
| 7,018,351 B1* | 3/2006 | Iglesias ............. A61F 5/0111 128/882 |
| 7,018,352 B2 | 3/2006 | Pressman et al. |
| D519,211 S | 4/2006 | Doty et al. |
| 7,077,818 B2 | 7/2006 | Ingimundarson et al. |
| 7,163,518 B1 | 1/2007 | Roche et al. |
| 7,163,519 B2 | 1/2007 | Price et al. |
| 7,182,743 B2 | 2/2007 | Slautterback et al. |
| D541,085 S | 4/2007 | Marsilio |
| 7,288,076 B2* | 10/2007 | Grim ............. A61F 5/0111 602/27 |
| 7,294,114 B1 | 11/2007 | Clement et al. |
| 7,303,538 B2 | 12/2007 | Grim et al. |
| 7,311,686 B1* | 12/2007 | Iglesias ............. A61F 5/0118 602/20 |
| 7,354,411 B2 | 4/2008 | Perry et al. |
| 7,384,584 B2 | 6/2008 | Jerome et al. |
| 7,475,501 B1 | 1/2009 | DeToro et al. |
| 7,563,238 B1 | 7/2009 | Breashears |
| 7,569,022 B2 | 8/2009 | Morinaka |
| 7,585,285 B2 | 9/2009 | Pone et al. |
| 7,597,674 B2 | 10/2009 | Hu et al. |
| 7,666,157 B2 | 2/2010 | Win |
| D616,556 S | 5/2010 | Hu |
| 7,727,173 B2 | 6/2010 | Rooney |
| 7,727,174 B2 | 6/2010 | Chang et al. |
| 7,743,532 B2 | 6/2010 | Bledsoe et al. |
| D619,726 S | 7/2010 | Win |
| 7,758,529 B2 | 7/2010 | Jensen et al. |
| 7,867,182 B2 | 1/2011 | Iglesias et al. |
| D634,438 S | 3/2011 | Hu |
| 7,896,826 B2 | 3/2011 | Hu et al. |
| 7,918,813 B2 | 4/2011 | Drake et al. |
| D640,792 S | 6/2011 | Anderson et al. |
| D641,084 S | 7/2011 | Anderson et al. |
| D642,695 S | 8/2011 | Anderson et al. |
| 8,002,724 B2 | 8/2011 | Hu et al. |
| D645,153 S | 9/2011 | Anderson et al. |
| 8,012,112 B2 | 9/2011 | Barberio |
| D662,598 S | 6/2012 | Anderson et al. |
| 8,226,585 B2 | 7/2012 | Pick et al. |
| 8,251,932 B2 | 8/2012 | Fout |
| 8,251,936 B2 | 8/2012 | Fout et al. |
| 2002/0062579 A1 | 5/2002 | Caeran |
| 2002/0128574 A1 | 9/2002 | Darby |
| 2003/0196352 A1 | 10/2003 | Bledsoe et al. |
| 2004/0015112 A1 | 1/2004 | Salutterback et al. |
| 2004/0030275 A1 | 2/2004 | Morinaka |
| 2005/0172517 A1 | 8/2005 | Bledsoe et al. |
| 2005/0228332 A1 | 10/2005 | Bushby |
| 2005/0240133 A1 | 10/2005 | Rooney |
| 2005/0274046 A1* | 12/2005 | Schwartz ............. A61F 5/0127 36/110 |
| 2006/0032093 A1 | 2/2006 | Vannini |
| 2006/0048344 A1 | 3/2006 | Cavanagh et al. |
| 2006/0084899 A1 | 4/2006 | Verkade et al. |
| 2006/0189907 A1 | 8/2006 | Pick et al. |
| 2006/0217649 A1 | 9/2006 | Rabe |
| 2007/0010770 A1 | 1/2007 | Gildersleeve |
| 2007/0191749 A1 | 8/2007 | Barberio |
| 2007/0260164 A1 | 11/2007 | Chiodo et al. |
| 2007/0276307 A1 | 11/2007 | Erenstone |
| 2008/0004558 A1 | 1/2008 | Outred et al. |
| 2008/0098626 A1 | 5/2008 | Wright |
| 2008/0154166 A1 | 6/2008 | Beckwith et al. |
| 2008/0294082 A1 | 11/2008 | Chang et al. |
| 2008/0294083 A1 | 11/2008 | Chang et al. |
| 2008/0302371 A1 | 12/2008 | Cohen et al. |
| 2008/0319362 A1 | 12/2008 | Joseph |
| 2009/0043234 A1 | 2/2009 | Bledsoe et al. |
| 2009/0076425 A1 | 3/2009 | Schwartz |
| 2009/0192427 A1 | 7/2009 | Brown et al. |
| 2009/0192428 A1 | 7/2009 | DeBoer et al. |
| 2009/0227927 A1 | 9/2009 | Frazer |
| 2009/0227928 A1 | 9/2009 | Drake et al. |
| 2009/0264803 A1 | 10/2009 | Darby, II et al. |
| 2009/0287127 A1* | 11/2009 | Hu ............. A61F 5/0111 602/27 |
| 2009/0299246 A1 | 12/2009 | Pone et al. |
| 2009/0306565 A1 | 12/2009 | Chan |
| 2010/0069807 A1 | 3/2010 | Cox |
| 2010/0100018 A1 | 4/2010 | Fout |
| 2010/0204631 A1 | 8/2010 | Rooney |
| 2010/0234782 A1 | 9/2010 | Hu et al. |
| 2010/0324461 A1 | 12/2010 | Darby |
| 2011/0015555 A1 | 1/2011 | Anderson et al. |
| 2011/0021963 A1 | 1/2011 | Graddon et al. |
| 2011/0066095 A1 | 3/2011 | Price et al. |
| 2011/0146032 A1 | 6/2011 | Hu et al. |
| 2011/0196275 A1 | 8/2011 | Chang et al. |
| 2011/0313336 A1 | 12/2011 | Chan |
| 2012/0000092 A1 | 1/2012 | Ingvarsson et al. |
| 2012/0010534 A1 | 1/2012 | Kubiak et al. |
| 2012/0010535 A1 | 1/2012 | Kubiak et al. |
| 2012/0035520 A1 | 2/2012 | Ingimundarson et al. |
| 2012/0065564 A1 | 3/2012 | Hoffmeier |
| 2012/0078148 A1 | 3/2012 | Hu et al. |
| 2012/0116275 A1 | 5/2012 | Pochatko |
| 2013/0066247 A1 | 3/2013 | Bird et al. |

FOREIGN PATENT DOCUMENTS

| | | |
|---|---|---|
| DE | 2341658 | 3/1974 |
| DE | 3228753 | 2/1984 |
| DE | 3909922 | 2/1990 |
| EP | 0095396 | 11/1983 |
| EP | 1006960 | 1/2003 |
| FR | 2399811 | 3/1979 |
| RU | 2165229 | 4/2001 |

OTHER PUBLICATIONS

Article from http://www.alimed.com regarding AliMed D2 Night Splint for Plantar Fasciitis.

Aircast Incorporated Product Brochure, "SP-Walker, short pneumatic walking brace", Jan. 11, 2002.

PCT Publication No. WO/2012/020251, dated Feb. 16, 2012, regarding PCT Application No. PCT/GB2011/051499.

(56) References Cited

OTHER PUBLICATIONS

PCT Publication No. WO/2005/097014, dated Oct. 20, 2005, regarding PCT Application No. PCT/SE2005/000513.
PCT Publication No. WO/2012/099989, dated Jul. 26, 2013, regarding PCT Application No. PCT/US2012/021763.
PCT Publication No. WO/2012/001678, dated Jan. 5, 2012, regarding PCT Application No. PCT/IL2011/000487.
Paul A. Dale, M.D. et al.; "A New Concept in Fracture Immobilization", Clinical Orthopaedics. Oct. 1993, vol. 295: 264-269.

* cited by examiner

OVERMOLDING FOR AN ORTHOPEDIC WALKING BOOT

CROSS-REFERENCE TO RELATED APPLICATION

This application claims the benefit of U.S. Provisional Application Ser. No. 61/801,843, filed on Mar. 15, 2013, and U.S. Provisional Application Ser. No. 61/916,077, filed on Dec. 13, 2013, each of which is expressly incorporated by reference herein in its entirety

BACKGROUND

Field

The present disclosure relates generally to orthopedic walking boots.

Background

It is common that people, especially active and/or frail people, experience a variety of lower leg and ankle injuries. To aid in the treatment of the injuries it is desirable to immobilize the injury, typically above and below the affected joint.

Physicians traditionally place a patient's leg in a short leg cast, which is a cast that begins at the patient's toes and ends below the patient's knee. Generally, casts retain heat, cause an itching sensation on the skin, and rub against the leg after swelling of the leg subsides.

An alternative to the short leg cast is an orthopedic walking boot, or a premanufactured orthopedic walking boot, that is made of a rigid plastic frame lined with a soft component (e.g, a soft padding) to accommodate the leg comfortably. Often, the liner, or soft component, may house a series of air bladders that can be adjusted by the patient to improve the fit and help compress the swelling to reduce pain and increase stability. The orthopedic walking boots can be removed to treat skin problems, such as, to remove sutures or conduct passive range of motion exercises. Short leg casts do not offer the luxury of easy on/off.

An orthopedic walking boot is primarily a rigid encasing that envelopes the leg and immobilizes the foot and ankle at a neutral position (e.g., the foot extends 90 degrees relative to the leg). The patient can walk easiest if the ankle is fixed at 90 degrees. At angles other than 90 degrees the patient will be walking on the toes or on the heel. The sole of the foot is generally curved from front to back in a rocker bottom fashion. The curvature of the sole provides a smoother stride from front to back allowing the heel to strike the ground first, followed by a rocking of foot forward, and finally a push off on the toes for a successful step.

SUMMARY

Aspects of a method of manufacturing an orthopedic walking boot may include providing a base configured to support a user's foot and receive a support assembly configured to support the user's lower leg; and overmolding an outer sole to the base.

Another aspect of a method of manufacturing an orthopedic walking boot may include providing a base configured to support a user's foot and receive a support assembly configured to support the user's lower leg; and integrally forming an outer sole to the base.

Another aspect of a method of manufacturing an orthopedic walking boot may include providing a base configured to support a user's foot and receive a support assembly configured to support the user's lower leg, the base comprising a section configured to support the user's posterior portion of the heel; and overmolding an outer sole and at least one of a heel cushion and heel bumper to the base using a single shot process with said at least one of the heel cushion and heel bumper being arranged with the section.

Another aspect of a method of manufacturing an orthopedic walking boot may include providing a base configured to support a user's foot and receive a support assembly configured to support the user's lower leg, the base comprising a first section to protect the forward end of the user's toes and a second section to support the user's posterior portion of the heel; mating a shock absorber insert with the base to provide shock absorption to the user's foot; and overmolding an outer sole, a toe bumper, a heel cushion and a heel bumper to the base using a single shot process; wherein at least a portion of the outer sole is overmolded to the base and the shock absorber insert, the toe bumper is overmolded to the first section, the heel cushion is overmolded to an interior portion of the second section, and the heel bumper is overmolded to the second section with at least a portion of the heel bumper arranged with an exterior portion of the second section.

DETAILED DESCRIPTION

Figure 1:
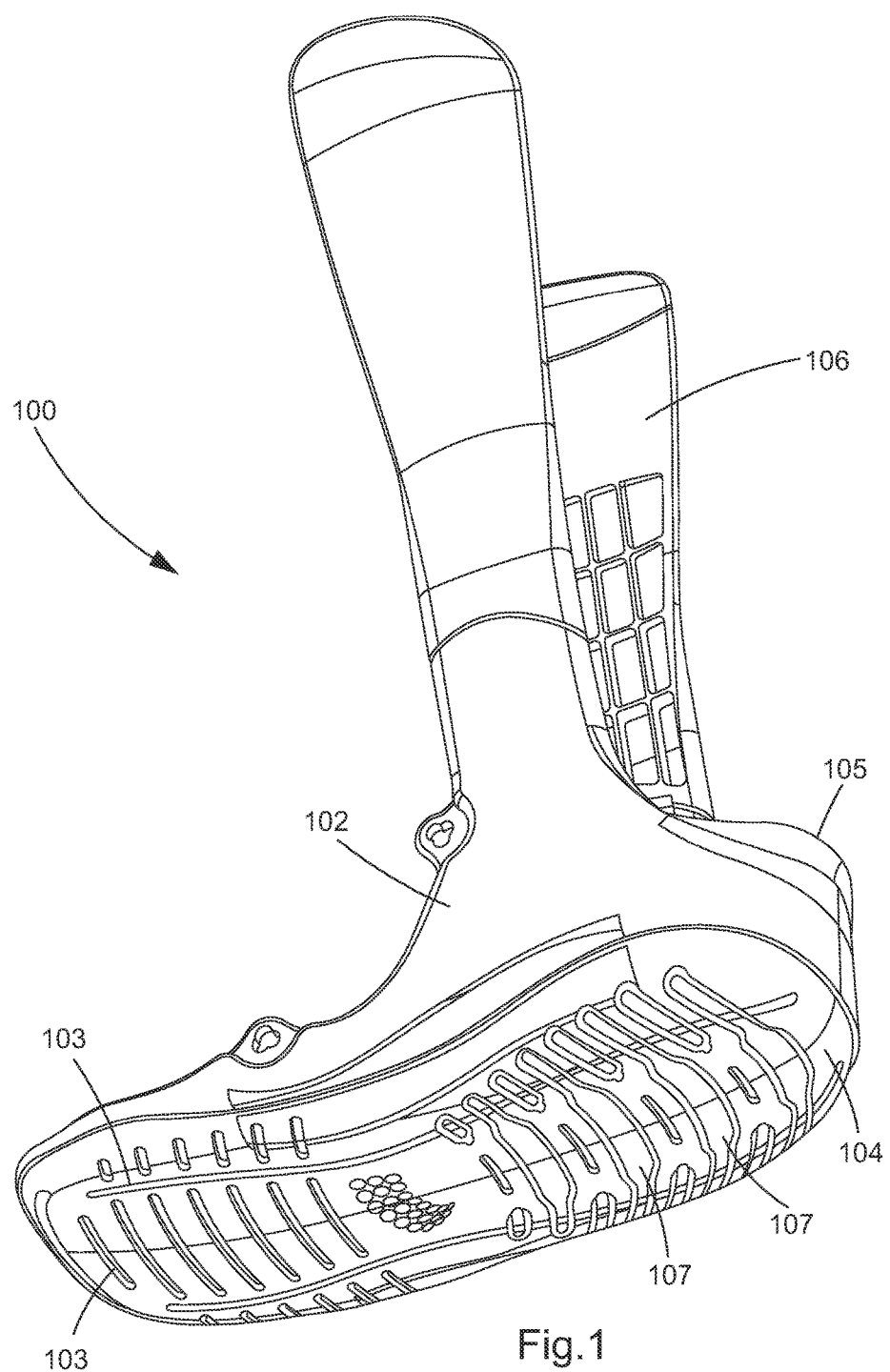
FIG. 1 is a perspective view of an orthopedic walking boot, in accordance with aspects of the present invention.

Various aspects of the present invention will be described herein with reference to drawings that are schematic illustrations of idealized configurations of the present invention. As such, variations from the shapes of the illustrations as a result, for example, manufacturing techniques and/or tolerances, are to be expected. Thus, the various aspects of the present invention presented throughout this disclosure should not be construed as limited to the particular shapes of elements (e.g., regions, layers, sections, substrates, etc.) illustrated and described herein but are to include deviations in shapes that result, for example, from manufacturing. Thus, the elements illustrated in the drawings are schematic in nature and their shapes are not intended to illustrate the precise shape of an element and are not intended to limit the scope of the present invention, unless intentionally described as such.

It will be understood that when an element such as a region, layer, section, or the like, is referred to as being "on" another element, it can be directly on the other element or intervening elements may also be present. In contrast, when an element is referred to as being "directly on" another element, there are no intervening elements present. It will be further understood that when an element such as a structure is referred to as being coupled to another element, it can be directly connected to the other element or intervening elements may also be present. Similarly, two elements may be mechanically coupled by being either directly physically connected, or intervening connecting elements may be present. It will be further understood that when an element is referred to as being "formed" on another element, it can be deposited, attached, connected, coupled, or otherwise prepared or fabricated on the other element or an intervening element.

Furthermore, relative terms, such as "lower" or "bottom" and "upper" or "top," may be used herein to describe one element's relationship to another element as illustrated in the drawings. It will be understood that relative terms are intended to encompass different orientations of an apparatus in addition to the orientation depicted in the drawings. By way of example, if the orientation of an orthopedic walking boot shown in the drawings is turned over, elements described as being on the "lower" side of other elements would then be oriented on the "upper" side of the other elements. The term "lower", can therefore, encompass both an orientation of "lower" and "upper," depending of the particular orientation of the orthopedic walking boot. Similarly, if the orientation of an orthopedic walking boot shown in the drawing is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The detailed description set forth below in connection with the appended drawings is intended as a description of various aspects of the present invention and is not intended to represent all aspects in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present invention.

Various aspects of the present invention may provide an orthopedic walking boot that may be fitted around the leg to provide support and allow ambulation for the affected limb.

Reference to various ranges may be used to describe certain aspects of the present invention. By way of example, a range may be used to describe variations of the bonding force at different points on an outer sole to describe an evenly distributed bonding of the outer sole to the base of the orthopedic walking boot. By way of an example, an outer sole which provides evenly distributed bonding to the base of the orthopedic walking boot may exhibit a narrower tolerance band of force values at all x,y coordinates on the bonding surface than tolerance band of any other attachment method of the outer sole to the base of the orthopedic walking boot.

People often experience injuries to the lower leg and ankle. For example, blunt trauma, sports injuries and common falls are the primary causes. Injuries such as fractures of the bones or soft tissue injuries (e.g., ligamentous tears) have similar symptoms. Swelling, pain and inability to ambulate without support are expected and predictable. Some injuries need to be immobilized for a period of time for the injury to heal. The time required for ligamentous injuries to heal is similar to the time required for fractures to heal. A period of 4 to 6 weeks of immobilization is common. Different injuries require different rehab times and regimes.

Aspects of the present invention are directed to orthopedic walking boots. In an aspect of the prevention invention, an orthopedic walking boot may include bilateral struts which connect a base of the orthopedic walking boot to an upper portion of the orthopedic walking boot. The struts may be rigid and provided on either side of the leg. The bilateral struts may be held onto the limb with strapping systems that encircle at least a portion of the limb. In another aspect, the base may be attached a posterior piece which extends from the foot to the back of the leg and calf forming a clamshell configuration. In the clamshell configuration, a single piece encompasses the side of the leg (similar to the bilateral configuration) as well as the rear of the leg. The orthopedic walking boot may include an adjoining anterior piece that joins or overlaps the posterior piece and is held on by a traditional strapping system or with mechanical attachment mechanism. In another aspect, the orthopedic walking boot may comprise a "hybrid" configuration (also referred herein as a "multi-sectioned" configuration). In the hybrid configuration, the base may be attached to the bilateral struts of the bilateral configuration and also attached a separate/non-integral posterior element that encompasses the rear of leg (similar to the rear portion of the clamshell). In this manner, the bilateral struts surround the side of the legs while the separate posterior portion encompasses the rear of the leg. Thus, the hybrid configuration achieves a similar result as the clamshell with multiple sections, hence, "multi-sectioned."

In an aspect, the orthopedic walking boot may be configured such that the portion that receives the user's foot (e.g., the base portion) extends at 90° degrees or at substantially 90° relative to a longitudinal axis of the portion that receives the user's leg (e.g., the upper portion). In another aspect, the orthopedic walking boot may include two struts rising from the base. The orthopedic walking boot may further include a soft component within the constraints of the struts and on top of the base. The soft component may be held by straps.

The orthopedic walking boot may include an outer sole overmolded onto the base. Traditionally, the soles of orthopedic walking boots are die-cut or molded separately from the base into the shape needed to mate with the base. Traditionally, the outer sole is then adhered onto the rigid walker by an adhesive. Traditionally, both the outer sole and the base of the rigid walker surface are treated with the adhesives. Attaching the separately formed sole to the base via an adhesive has several problems. Adhesives can be difficult to apply, have a limited shelf life, are affected by humidity or temperatures, and have a variety of set times. Furthermore, it can be difficult to apply additives to all desired surfaces. Often, there is an over spray of adhesives when precise metering is difficult. Manufacturers may apply too much adhesive which results in failed or reduced joining and external leakage or inconsistent curing. Conversely, insufficient adhesive can result in failures. The adhesives have to be correctly applied in a controlled environment for the high shear and peel strength to be accomplished predictably in a medical grade product.

Furthermore, there is a growing awareness regarding the toxicity of many adhesives and for using them in medical products placed next to the skin or close to wounds and broken skin. Additionally, it is nearly impossible to thoroughly test the bond strength when a sole is attached to a base via an adhesive. Since the outer sole is fully attached to the base, it is impossible to visually identify where the adhesive is located as compared to where it is supposed to be. Only destructive testing can provide the necessary information. Adhesives are often applied manually by humans, allows for human error.

The problem of adhesives peeling is of particular concern for orthopedic walking boots because, unlike footwear, if the outer sole of an orthopedic walking boot begins to separate from the base, a patient cannot easily replace or repair it. Because the orthopedic walking boot protects a fractured leg, a patient is not able to take the time necessary to remove the orthopedic walking boot and repair it. Due to the shuffling gait patterns that many patients initially exhibit, the toe portion of the orthopedic walking boot walker is placed under long-term extreme shear and peel forces which are difficult for adhesives to withstand. Therefore, with adhesives the tip or the toe of the outer sole may begin to separate during use. Every time the toe shuffles, the soft outer sole is forced to stretch and deform as compared to the base it is attached to. As this happens, the separating outer sole may catch onto the surface the patient is walking upon, which can cause the patient to trip and fall.

In an effort to ensure a more aggressive, permanent, predictable and safe attachment of an outer sole to the base, one aspect of the present invention includes a method of attaching the outer sole directly onto the base of the orthopedic walking boot by overmolding, e.g., without the need for an adhesive. Overmolding ensures a permanent bond because the process molds the outer sole under high heat and pressure directly onto the base of the orthopedic walking boot. No separate adhesive layer is needed between the outer sole and the base. Overmolding provides a permanent chemical joining of the two materials such that the outer sole is integrally formed with the base. This arrangement provides high peel and shear strength.

Overmolding is a process of injection molding one material onto a second (typically rigid plastic) to achieve a combination of properties (mechanical, aesthetic, etc.) in specific zones, often resulting in an integral bond between the two materials. Overmolding is stronger, safer, and more consistent than other attachment method such as an adhesive, and has a lower long-term cost. The majority of the overmolding described herein will pertain to the outer sole of the orthopedic walking boot, i.e., the soft underside of the orthopedic walking boot that contacts the floor as the patient walks. In an aspect of the present invention, the overmolding process includes placing the base into a die (also referred herein as "mold"). The die may be particularly shaped to receive the base and to inject molten resin precisely where desired. Once the base is secured in the die, the molten resin is injected into the mold and flows around precise portions of the base. The flow of resin may be restricted by the geometry of the die. Once the resin hardens, the base, having the outer sole overmolded onto it, may be removed from the die.

The outer sole may be overmolded to the base such that the outer sole is continuous (FIG. 1) or segmented (FIG. 4). The outer sole may be molded at a different time than the base. In addition, the base and the outer sole may be molded within a very short interval of time between each other while the base is still warm, which in turn can increase the surface acceptance of the outer sole to the base. The outer sole may be made of a material that is chemically compatible with the base of the orthopedic walking boot.

In an aspect, the outer sole may be applied to the base of the orthopedic walking boot to ensure a continuous, or near continuous surface for the patient to pivot upon while turning during ambulation. Furthermore, a plurality of through-holes may be distributed on the bottom surface of the base, which is discussed in more detail below. After the outer sole has been overmolded to the base, a tool may be inserted and pressed against the inside surface of the outer sole to determine peel strength and shear strength. Furthermore, an undercut around the perimeter of the base may secure the outer sole mechanically from removal in a direction normal to the base (i.e., a force pulling the outer sole off the base).

Another aspect may include overmolding the outer sole onto an orthopedic walking boot having a bilateral strut configuration, a clamshell configuration, or a hybrid configuration. The overmolding provides a safe way to attach the outer sole to the base of the orthopedic walking boot without using an adhesive to connect the outer sole to the base. In another aspect, the orthopedic walking boot may comprise a posterior splint that is removable and attached to the posterior component of the orthopedic walking boot. For this type of orthopedic walking boot, overmolding of the outer sole to the base of the orthopedic walking boot may be accomplished in the same manner discussed above.

As discussed above, an aspect of the present invention includes an orthopedic walking boot with an outer sole that is bonded to the base of the orthopedic walking boot without an adhesive. FIG. 1 illustrates an orthopedic walking boot 100 with an outer sole 104 which may be overmolded to the base 102 of the orthopedic walking boot 100. The outer sole may be elastomeric. The orthopedic walking boot 100 may include a support assembly 106. The support assembly 106 shown in FIG. 1 is the bilateral type. However, the orthopedic walking boot may have support assemblies consistent with the clamshell or hybrid types discussed above.

FIG. 1 illustrates an outer sole 104 that may completely cover the bottom surface of the base 102, and in particular, portions of the base 102 that contact the ground during use. The outer sole 104 may extend up the sides of the perimeter of the walker base 102 to maximize surface contact between the outer sole 104 and the base 102. In an aspect, the outer sole 104 may comprise a thermoplastic elastomer bonded by overmolding to the base 102. The base 102 may comprise a rigid polypropylene material. Alternatively, a number of different material pairs may be bonded in a similar manner, as long as they are chemically and thermally compatible. The bottom surface of the outer sole 102 may include tread 103 formed during the overmolding process. Various tread patterns may be applied by using a series of inserts in the overmold tool, where each insert is designed aesthetically or otherwise, to provide a different appearance of the tread while maintaining the desired physical properties, e.g., water channeling, grip on slippery surfaces, etc. Furthermore, the longitudinal axis of the outer sole 104 may be defined as the axis along the direction from the heel of the outer sole 104 to the toe of the outer sole 104. The outer sole may further include apertures 107 formed during the overmolding process similar to the tread.

Figure 2:
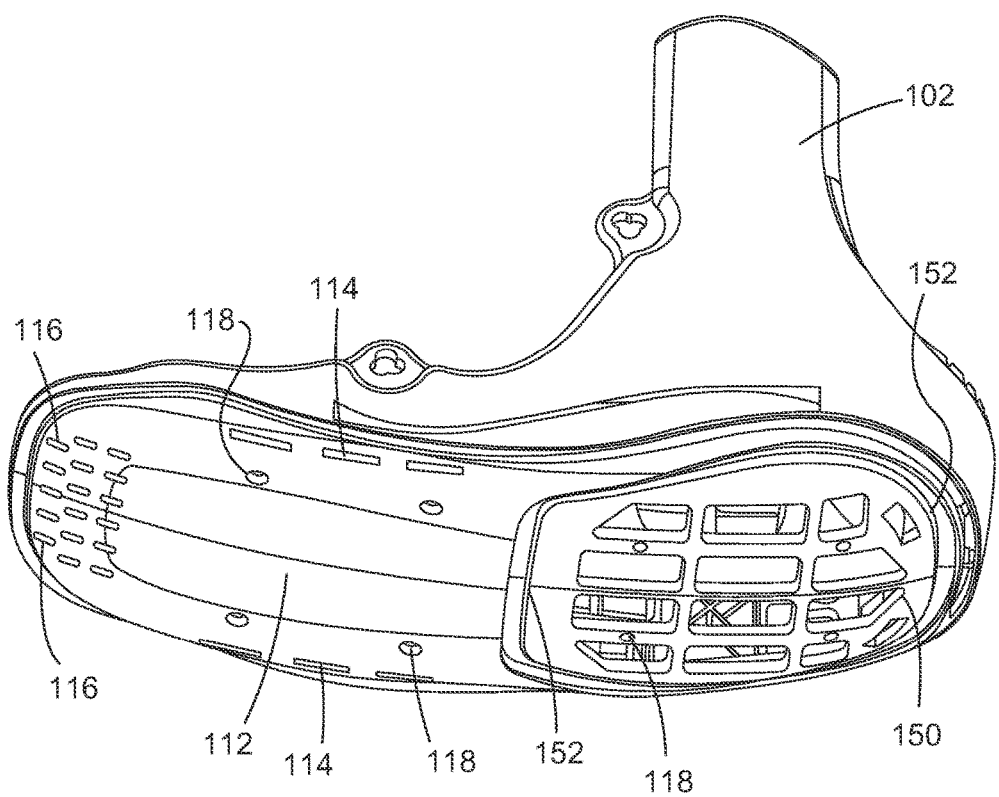
FIG. 2 is an bottom perspective view of a base of the orthopedic walking boot of FIG. 1, without an outer sole.

FIG. 2 is shows a bottom perspective view of the base 102 of the orthopedic walking boot prior to overmolding the outer sole onto the base. FIG. 2 illustrates one aspect of the base 102 which utilizes a plurality of fastening techniques to secure the outer sole to the base 102 via overmolding. The base 102 may include a substrate section 112 having a substantially smooth surface. The smooth surface facilitates flow of the outer sole resin material longitudinally from front to back (e.g., heel to toe) during the overmolding process. The smooth quality of the base substrate section 112 has a low surface roughness which allows for less turbulence in the resin at the substrate surface, allowing for the superior surface adhesion. The chemical bond between the substrate and the overmolded material in this case represents a high peel strength type of adhesion.

The base 102 may include first blind holes 114 passing partially through the thickness of the base substrate section 112. In another aspect, the holes 114 may be through holes that pass entirely through the base 102. As shown in FIG. 2, the geometry of the blind holes 114 may be rectangular. The blind holes 114, passing partially through the thickness of the base substrate, allow the outer sole resin material to fill into the holes during the overmolding process and chemically bond to the inside surface of holes. As shown in FIG. 2, the blind holes 114 may be disposed adjacent the periphery of the substrate section 112. The blind holes 114 may have a substantially rectangular shape that extends in the direction of the flow of the outer sole resin material during the overmolding process (e.g., in a direction from heel to toe). When the resin material adheres to the inside surface of the blind holes 114 it creates a shear-type connection to the base. This connection is a significantly stronger type of bond than a peel-type bond that adhesion alone would provide.

The geometry of the blind holes 114 required to provide an adequate shear bond is not limited to a rectangular geometry described above and is only one of a number of appropriate shapes that will provide the proper bond. The particular geometry may depend on the flow characteristics of the selected overmolding resin, and may include stepped walls, circular or non-circular holes, and/or other geometry. Orientation of the hole geometry with respect to the surrounding geometry of the orthopedic walking boot may be determined by the loading conditions anticipated in a particular area. Specifically, in an aspect, the holes may include linearly extending holes at varying angles relative to the primary axis extending along the length of the orthopedic walking boot (i.e., from heel to toe). The linear holes may provide strength to the overmold in an area of the base where patients drag or rotate more than in other zones, thus providing an elevated amount of applied stress to the overmolded outer sole in that area.

Similarly, the spacing from one hole to another may vary depending on the manner in which the orthopedic walking boot is used. The spacing may be determined based upon use patterns (e.g., a pattern that indicates which portion of the sole has heavier wear during use of the orthopedic walking boot). For example, the placement of linear holes may be denser in areas of base that correspond to portion of the sole that experience higher stress during uses. Additional aspects may include linear holes that are less densely distributed in areas of the base where peel adhesion alone is sufficient, while having a higher density of linear holes in areas of the base where more wear occurs.

It should also be noted that in other types of plastic molding, a generally accepted practice of "steel-safe" design can reduce the risk that pairs of parts intended to mate fit correctly, by adjusting the sizing after the mold has been tested. The shear features as described above make use of this principle, by reserving appropriate real estate such that additional shear holes may be added if testing shows the need for a more secure bond.

The base 102 may further include second blind holes 116 that perform a similar function of a providing a shear-type bond when the overmold resin flows over the surface of the base. The series of second blind holes 116 in the base (for example at the toe section as shown) similarly do not pass entirely through the base substrate 112, and therefore do not need to be shut off by the steel on the core side of the injection mold at the opposite side as the holes 116. In addition, the density of the blind holes 116 creates a locally stronger shear-type bond while maintaining the strength of the base substrate 112 in this area. The high density of these shear features is useful in the particular region shown, because the region near the toe exhibits a relatively high amount of wear when high mobility patients drag the toe of the orthopedic walking boot, or shuffle aggressively, for example. The specific geometry and spacing may be optimized based on the flow characteristics of the resin being injected. The specific geometry, spacing and orientation of the shear feature shown in FIG. 2 is one possible configuration, which may address unique concerns in specific zones of the walker, including high wear or areas of more frequent impact, etc. Those skilled in the art may derive similar configurations for geometry, spacing and orientation that address similar concerns.

Referring to FIG. 2, the base 102 may include through holes or apertures 118 which pass entirely through the base. The through holes 118 increase in diameter or overall cross section at an elevation away from the bottom surface of the base and into the base substrate 112. The resulting geometry of the hardened resin creates a physical interference or interlock which resists separation of the outer sole from the base. Thus, the physical interference serves a similar function as a nail used to secure a sole to a base.

Figure 3:
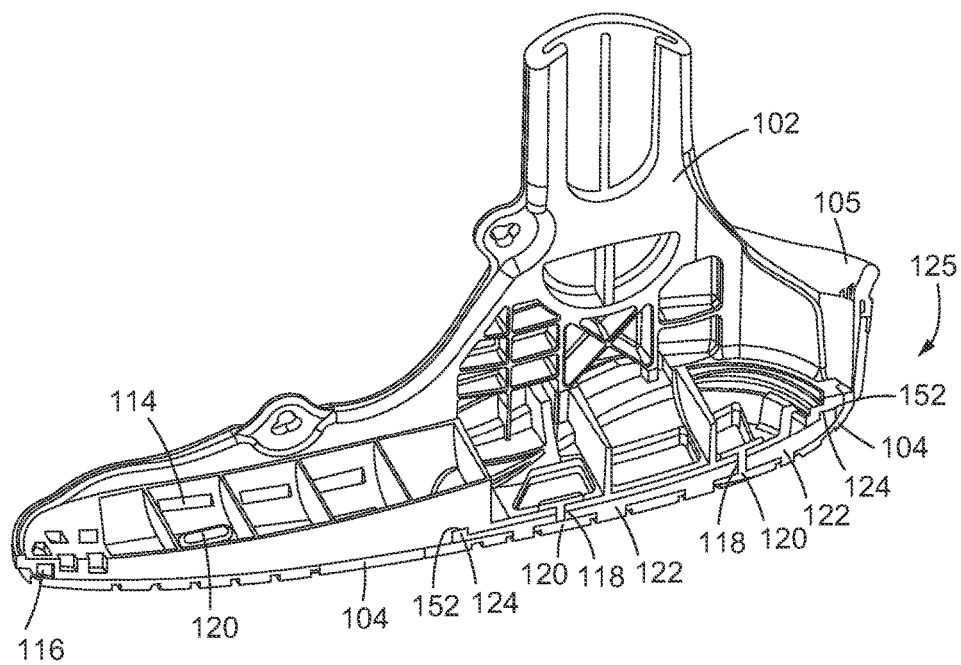
FIG. 3 is cut perspective view of the orthopedic walking boot of FIG. 1.

FIG. 3 shows a cut view of the base 102 of the orthopedic walking boot after the outer sole 104 has been overmolded onto the base 102. As best seen in FIG. 3, the base 104 may include a section 125 configured to support the user's posterior portion of the heel. FIG. 3 shows through holes 118 providing the entry point of the molten overmold material resin on the bottom surface side of the orthopedic walking boot 100. FIG. 3 further shows one example of the interlock 120 between the base 102 and the outer sole 104. For example, as shown in FIG. 3, a portion of the outer sole (i.e., a portion of the resin) extends from an outer surface of the base 102 into an inside surface of the base 102, thereby forming the interlock 120. This interlock 120 serves a similar function as a nail.

While FIGS. 2 and 3 show several example locations of through holes 118 (and thus locations of the mechanical interlocks 120 after overmolding), the through holes 118 can vary and size and position. It should also be noted that the larger cross section of the mechanical interlock feature 120, as compared to the throat, does not have to rest entirely above the wall of the base substrate 102. It may be configured such that the hole in the base substrate 102 is a chamfered hole, with the larger part of the resin still captured within the thickness of the wall section, such feature not needing to emerge above the floor of the base substrate 102 since the mechanical interlock is contained entirely within the thickness of the wall.

In an aspect, the outer sole may have a variety of colors by changing the color of the overmold resin in the hopper of the injection molding machine. This may be done on demand thereby reducing the need to inventory many outer soles as would be necessary if the soles were molded as a separate part that is then mechanically or adhesively attached to the base at a later time. This results in more flexibility of inventory and just-in-time manufacturing and lower ultimate cost.

As shown in FIGS. 2 and 3, the base 104 may include a pocket 150 (FIG. 2) for receiving a shock absorber insert 122 (FIG. 3). The perimeter of the pocket 150 may be defined by a receiving channel 152. The channel 152 is configured to receive a lip 124 of the shock absorber insert 122. The orthopedic walking boot may further include the shock absorber insert arranged with the base and the outer sole to provide shock absorption. The shock absorber insert may be arranged along a section of the base configured to support the user's plantar portion of the heel. As shown in FIG. 2, several of the through holes 118 may be disposed in pocket 150 of the base 104. These apertures located at the pocket may cooperate with corresponding through holes of the shock absorber insert. In another aspect, the through holes may not be present in the pocket area, in which case a shock absorber insert may be adhered within the pocket via an adhesive. The base portion in the pocket area may further include posts (not shown) extending from the underside surface of the base and extending in a direction toward ground/away from the bottom of the users foot. Similarly, the shock absorber insert may include corresponding receiving portions to mate with the posts. The mating of the posts with the receiving portions provide further stability of the shock absorber insert within the pocket.

In an aspect, the outer sole may comprise a first durometer, and the shock absorber insert may comprise a second durometer lower than the first durometer of the outer sole. For example, the shock absorber insert may have a Shore A durometer of 30 while the outer sole may have a Shore A durometer of 60.

Figure 4A:
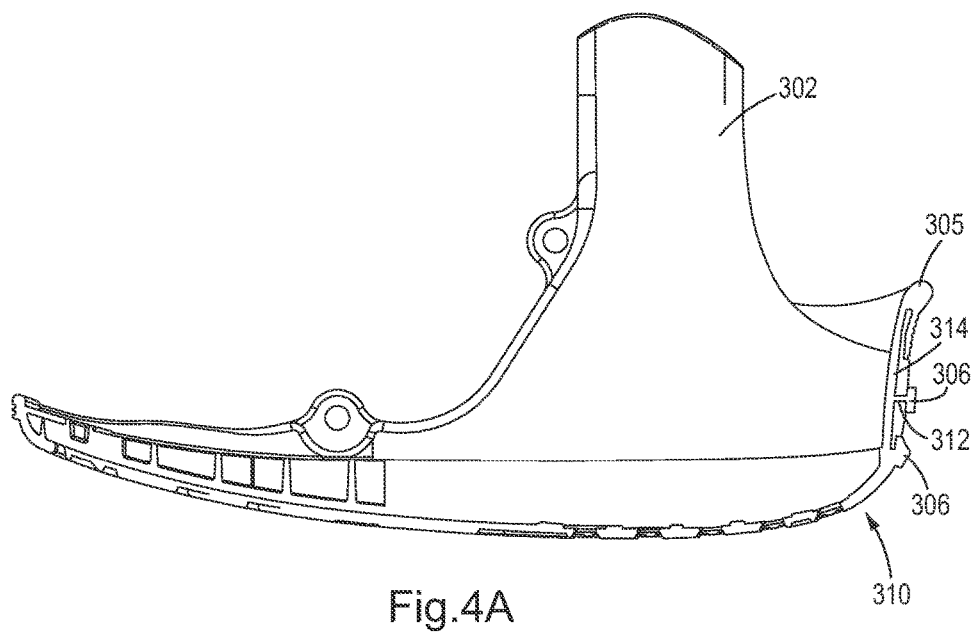
FIG. 4A is a side view of a base of an orthopedic walking boot in accordance with other aspects of the present invention.
Figure 4B:
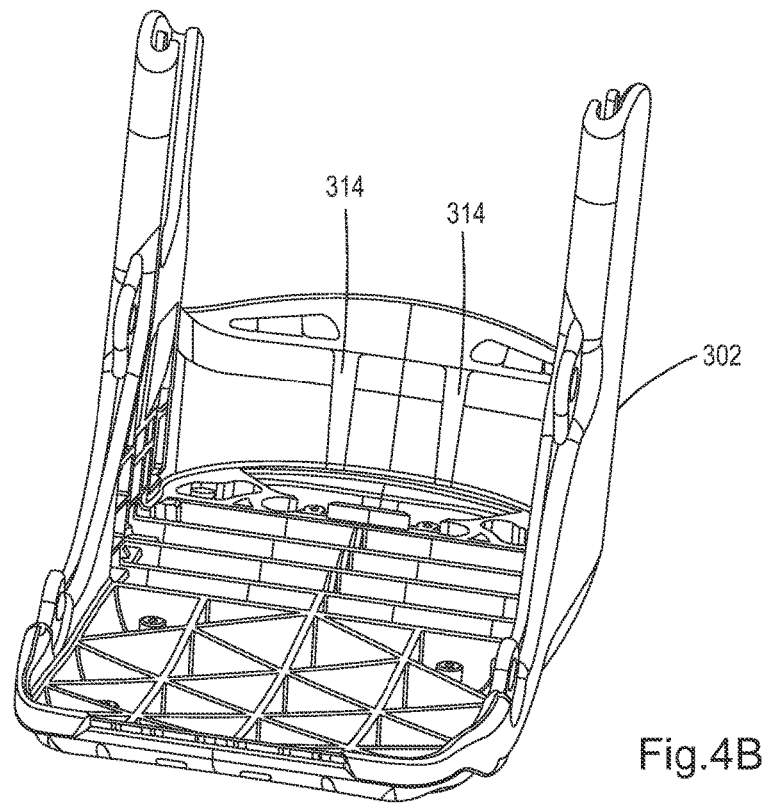
FIG. 4B is a top perspective view of the base of FIG. 4A prior to overmolding.

In another aspect, as shown in FIGS. 1 and 3, the orthopedic walking boot may include a heel cushion 105. In another aspect, as shown in FIG. 4A, the base 302 may include a heel cushion 305 and a heel bumper 306. The heel bumper may protrude from the heel portion 310. In an aspect, the heel portion of the base may have an aperture 312 extending through the thickness of the heel and communicating with a connective tunnel 314 that extends to the bottom surface of the base. FIG. 4A shows the resin material filled in the aperture 312 and the connective tunnel 314. FIG. 4B shows the base 302 prior to the molding process. As shown in FIG. 4B, prior to the molding process, the connectives tunnel 314 would not contain the solidified resin.

As noted above, the base 104 may include a section configured to support the user's posterior portion of the heel. In an aspect, the heel cushion 105 may extend along an interior portion of the section of the base configured to support the user's posterior portion of the heel. The molding of the outer sole and heel cushion may be performed such that the outer sole and the heel cushion comprise a continuous material overmolded to the base. In this case, the connective tunnel formed in the heel portion of the base provides a passageway for the resin to flow up the connective tunnel and solidify into the heel cushion. In another aspect, the outer sole and the heel bumper comprise a continuous material. In this case, the resin flows up the connective tunnel, into the aperture, and the hardened resin will form the bumper. In another aspect the outer sole, the heel cushion, and the heel bumper comprise a continuous material. In this case, the resin would flow up the connective tunnel to form the heel cushion and through the aperture to form the bumper.

Figure 5:
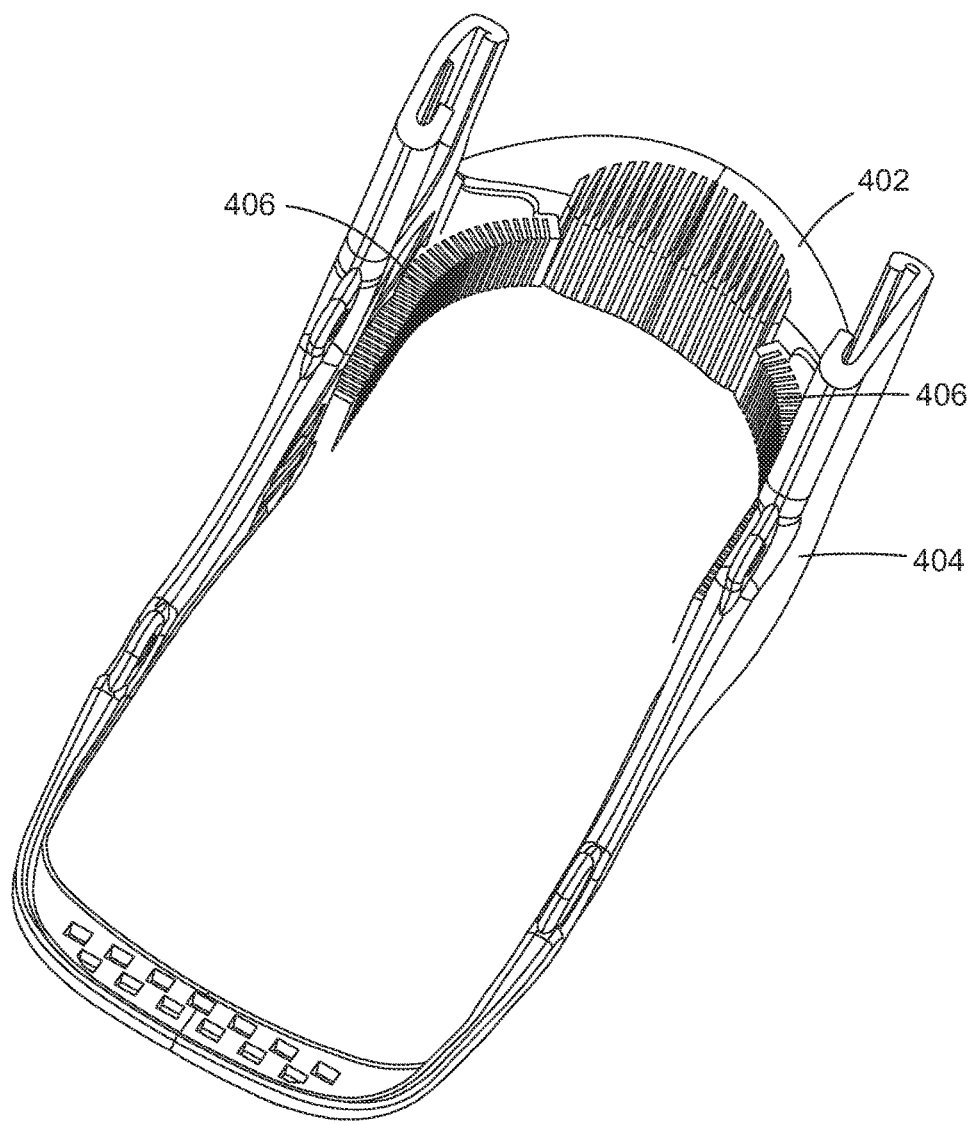
FIG. 5 is a top perspective view of a base of an orthopedic walking boot in accordance with other aspects of the present invention.

Furthermore, the heel cushion may extend along the interior portion of the section of the base configured to support the user's posterior portion of the heel. FIG. 5 shows a top perspective view another aspect of the present invention of a base 404 having a heel cushion 402 extending to the left and right lateral sides 406 of the base 404. A rear section (also referred herein as "distal section") of the base 404 is shown in a configuration where the soft heel cushion 402 extends to the left and right lateral sides 406 of the inside of the base 404, providing additional cushion for patient physiology. In other words, the heel cushion may be arranged with a section of the base to engage the user's posterior portion of the heel and may wrap around a distal end of the section of the base. The heel cushion may also extend along an interior portion of the section of the base between distal and proximal ends thereof.

Aspects of the present invention include a method of manufacturing an orthopedic walking boot. The base may be formed through injection molding by injecting a first material into a mold. Next, the outer sole may be overmolded on the base. The base may be provided within a mold, and the overmolding of the outer sole may include injection a material into the mold and allowing the material to form to the base. The overmolding of the outer sole may include injecting a second material into the mold and allowing the second material to form to the base. The shock absorbing insert may be overmolded to the base. In an aspect at least a portion of the outer sole is overmolded to the base through the shock absorber insert. The method may include overmolding a heel cushion to an interior portion of heel of the base. The outer sole and the heel cushion may comprise a continuous material overmolded to the base using a single shot process. Additionally, the outer sole and the heel bumper may be overmolded to the base using a single shot process.

Figure 6:
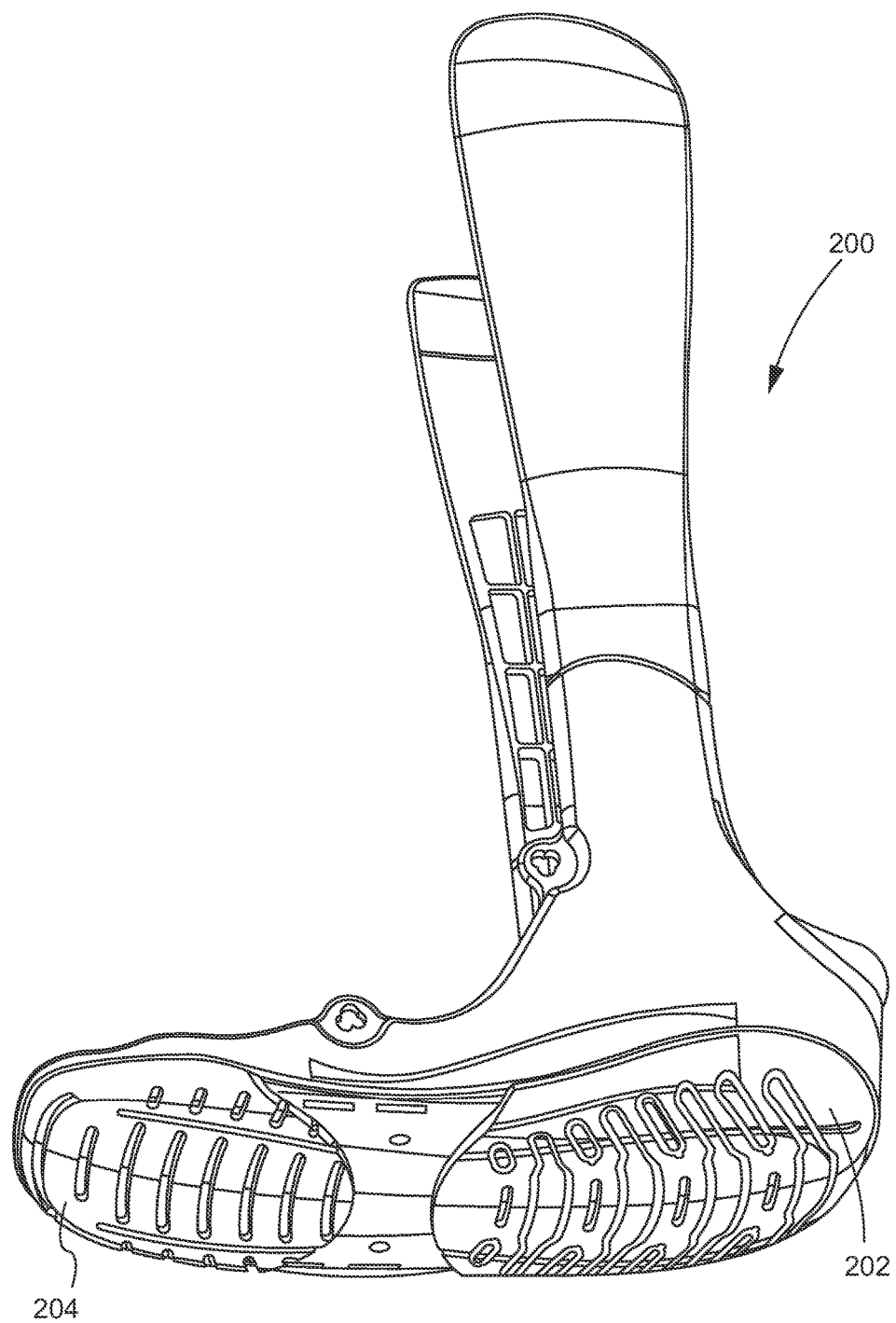
FIG. 6 is a perspective view an orthopedic walking boot, in accordance with other aspects of the present invention.

In another aspect, the outer sole may be non-continuous. FIG. 6 is a perspective view of an orthopedic walking boot 200 comprising of an outer sole overmolded in a plurality of overmolded sections 202, 204. By forming the outer sole in discrete sections, different materials can be used for each section, and therefore, different properties can be exhibited. For example, the different materials may have different colors, strengths, rigidity, grip, durometers, and the like.

To overmold two different sole sections, several methods may be used, including dual shot molding, where one material is molded onto the substrate, after which a second injection molding cavity is shuttled into position, and a second material is injected to be in contact with the substrate as well as the previously overmolded material. In another process, co-molding, the first material is shot into the mold containing the rigid substrate, while a movable part of the tool prevents material from entering a certain area. Once material is cured, the movable section of the tool changes position, and a new material is injected into the newly formed void, making bonding contact with the rigid substrate as well as the previously shot material. In a further aspect, two separate overmold tools are utilized.

In a further aspect, an outer sole section with one of the desired material properties (such as high-grip) is molded separately, and is placed against the substrate in the overmold tool. When the second material is injected into the mold, it bonds to both of the substrates that are in the tool. The result is an outer sole with two separate material properties.

Figure 7A:
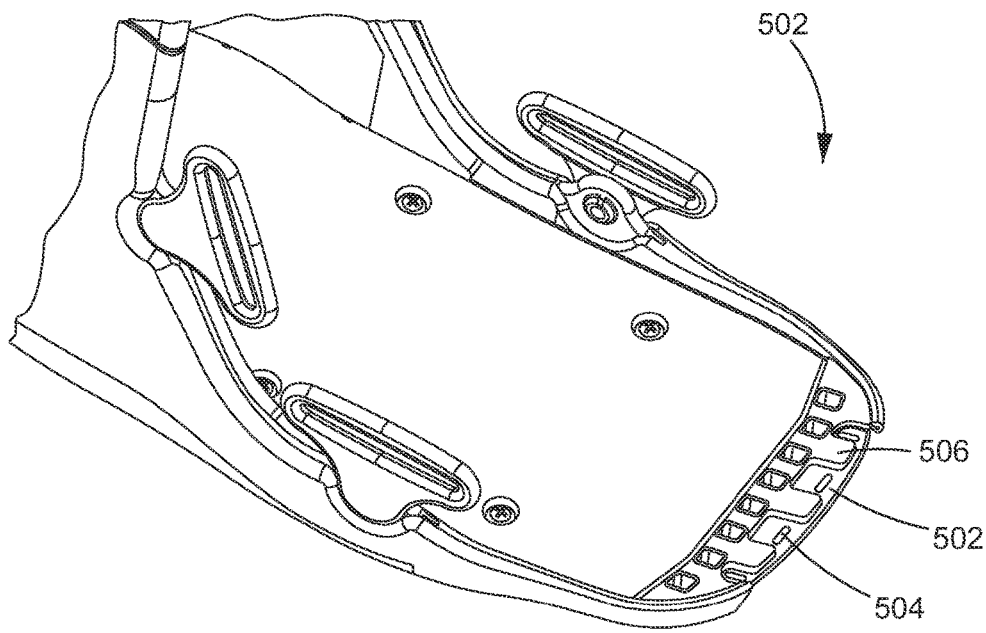
FIG. 7A is a partial perspective view of a base of an orthopedic walking boot prior to overmolding, in accordance with other aspects of the present invention.
Figure 7B:
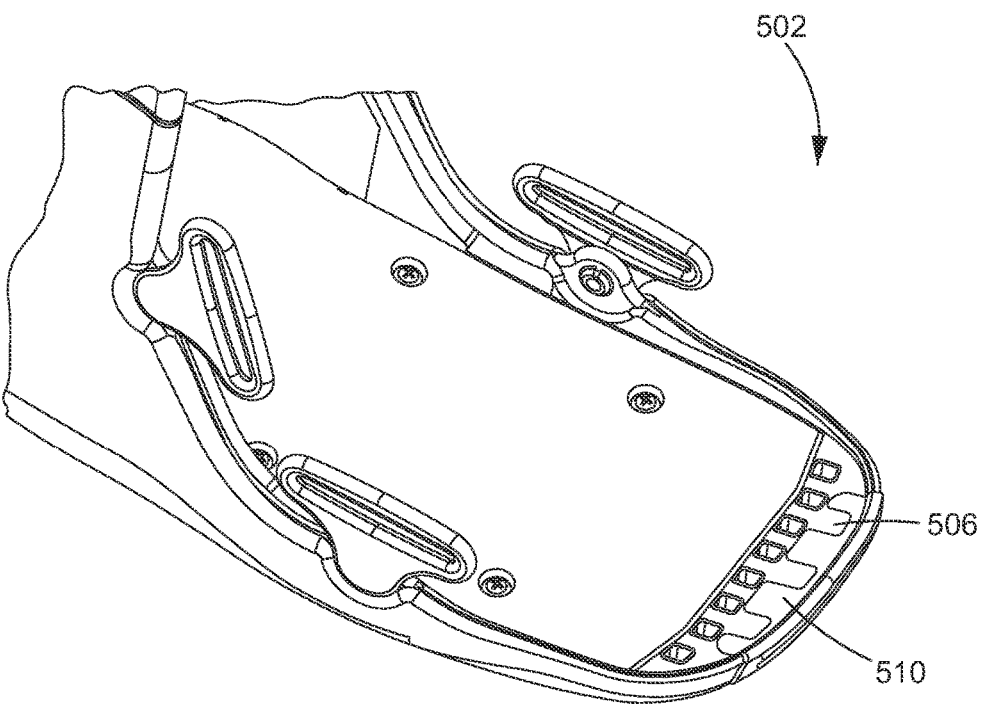
FIG. 7B is a partial perspective of the base of FIG. 7A after overmolding.

FIG. 7A is a partial perspective view of a base 502 of an orthopedic walking boot, prior to overmolding the outer sole to the base 502. As shown in FIG. 7A, prior to overmolding the outer sole to the base 502, the portion of the base 502 that protects the toe of the user during use may include a plurality of through holes 504. The plurality of through holes may extend entirely through the base 502. The through holes 504 may be separated from each other by a plurality of separators 506. As shown in FIG. 7A, the separators 506 may be disposed on top of the surface of the base that the through holes 504 extend through, Thus, the through holes reside is a smaller thickness portion 308 of the base relative to the separators 506. During overmolding of the outer sole, a portion of the resin material will flow through the through holes 504 an fill in the reduced thickness portion 508. FIG. 7B is a partial perspective view of the base 502 after overmolding the outer sole to the base 502. As shown in FIG. 7B, after overmolding, the base 502 may include a toe bumper 510. The toe bumper is formed when the molten resin material flows through the through holes 504, fills the reduced thickness portion 508, and then hardens. Thus, the toe bumper 510 may be overmolded on to the base. In an aspect, the toe bumper 510 can be overmolded onto the base separately or at the same time as overmolding the outer sole onto the base. When the resin of the outer sole passes through the through holes to form the toe bumper, the toe bumper is continuous with the outer sole. The method of manufacturing the orthopedic walking boot may include overmolding a toe bumper to a toe protecting section of the base. The outer sole and the toe bumper may be overmolded to the base using a single shot process.

The through holes in the toe protecting section of the base that allows for the toe bumper to be overmolded onto the base may also be applied to any of the aspects described above. For example, the through holes may be provided in the base shown in FIG. 2. Accordingly, by using a base having the holes for bonding the resin material to form the outer sole, the connective tunnels to allow the resin to form the heel cushion, the aperture through the heel portion to allow the resin to form the heel bumper, and the holes in the toe portion to allow the resin to form the toe bumper, one can form all of the outer sole, heel cushion, the heel bumper, and the toe bumper with a continuous material and with a single injection.

Figure 8:
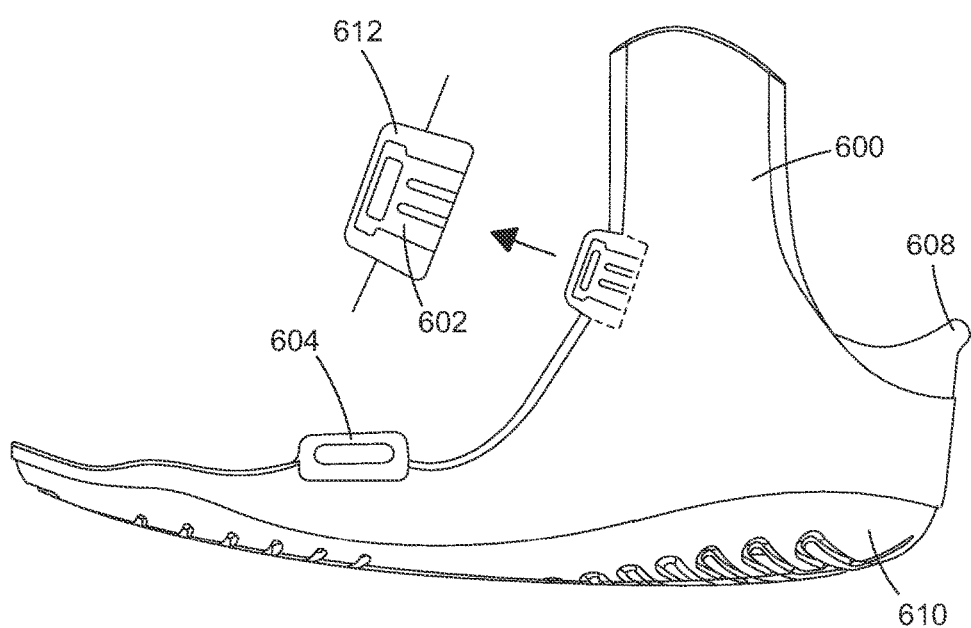
FIG. 8 is a side view of an orthopedic walking boot, in accordance with other aspects of the present invention.

FIG. 8 shows a base 600 of an orthopedic walking boot having a strap fastener 602, 604 and heel cushion 608. The strap fasteners 602, 604 have a region of overmolding directly adjacent to the strap holding feature. This boundary includes a region made with a material having a substantially lower modulus of elasticity, and allows for flexible controlled movement that would not be provided with other means of geometry. The strap fasteners 602, 604 may be fabricated separately to include an overmolded flexible zone, and then attached via conventional means including adhesives, fasteners etc. The use of the overmolding material elsewhere in the orthopedic walking boot allows for the use of flexible material in the area of the strap connectors 602, 604. FIG. 8 includes a blown-up portion of the strap connector 602. As shown in FIG. 6, overmolding 612 surrounds the strap fastener 602. Strap fastener 604 may comprise a different structure than strap fastener 602.

In addition, other elements of the orthopedic walking boot may be fastened by engagement or encapsulation with a soft overmolded material which may be used elsewhere in the design. These features may be parts or assemblies that are not intended to be removed and may be connected via conventional fastening methods. By way of example, FIG. 8 shows an orthopedic walking boot with an overmolded outer sole featuring a rigid insole, said insole assembled permanently to the rigid base by the interference created between the softer overmold material originating from the outer sole of the orthopedic walking boot, as the outer sole overmold material is channeled up through tunnel features in the rigid base to engage with the insole part.

In an aspect of the present invention, prior to overmolding, a piece of plastic softer than the base may be adhered to the bottom surface of the base. The base with or without the added softer plastic piece may then be placed inside a steel injection molding tool that has been preheated to an operating temperature that will facilitate the flow of the resin. One half of the injection molding tool comprises the cavity. When the tool is in the closed position in captures the base and holds it securely under pressure at predetermined locations. The pressure being applied particular locations serves to confine the resin material to the proper locations, and also may prevent deflection of portions of the base geometry that would otherwise occur due to the high pressure necessary inside the mold to push the molten resin throughout the tool. The cavity also defines the volume of space where the overmold material is desired.

After the mold is closed, the molten resin is injected into the mold with a specific injection speed and injection pressure (also referred herein as the injection cycle). The injection pressure is then held for a period of time while cooler liquid is circulated through pipes inside the steel adjacent to, but not in contact with the resin itself. Next, the cavity part of the tool moves to an open position where the base, with resin overmolded onto it, is ejected from its position in the tool (also referred herein as the ejection cycle).

The particular combination of injection speed and injection pressure has a direct impact on the properties of the final molded product such as bond strength, aesthetics, and surface geometry. For example, the resin can be heated to a particular temperature to facilitate the correct flow of the molten resin when inside the mold.

With respect to bond strength, the injection speed and hold time, and injection pressure may be chosen to ensure optimal bond strength between the base and the overmolded resin. Another aspect that that affects the bond strength is the surface finish of the finish bottom of the base, which may be optimally polished. For example, the bottom surface of the base (for example substrate section 112 shown in FIG. 2), may have a polish of at least B-2 as determined by Society of the Plastics Industry (SPI) Guidelines.

Additionally, the location of the injection gate in the tool is a factor that affects the minimum level in turbulence experienced by the resin as it fills the mold.

With respect to aesthetics, maintaining specific overmold parameters can avoid poor aesthetics. If the hold pressure of the overmold process is insufficient, visible surfaces overmold surfaces may become wavy or bumpy. If the injection and hold pressures are beyond certain limits, the overmold may travel past the intended boundaries, resulting in an inferior product. Also, careful monitoring of the temperature of the barrel of the injection machine will prevent excessively heated resin from causing thin portions of the base to detach and/or melt, would result in visible discoloration to the overmold.

The operating parameters may vary depending on the particular size of the base being used in the mold. The following example parameters are for a thermoplastic elastomeric. Example injection temperatures may include 23° C. to 25° C. Example cycle times may include 85 seconds to 88 seconds. Example pressure may include 45 Mpa to 80 Mpa. Example injection speeds (as percent of max speed) may be 43% to 78%. Example temperatures of the barrel may include 210° C. to 215° C.

When including the shock absorber insert in the orthopedic walking boot, additional steps may be performed. The shock absorber insert is first mated with the pocket of the base as described above. This assembly may occur in the cavity of the molding tool such that fingers pass through voids in the base to push against inside surfaces of the shock absorbing insert. The steel fingers perform the function of keeping the shock element in position without collapsing under the pressure of the injected resin.

The claims are not intended to be limited to the various aspects of this disclosure, but are to be accorded the full scope consistent with the language of the claims. It is noted that specific illustrative embodiments of the invention have been shown in the drawings and described in detail hereinabove. It is to be understood that various changes and modifications may be made without departing from the spirit and scope of the invention. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of manufacturing an orthopedic walking boot, comprising:
   providing a base configured to support a user's foot and receive a support assembly configured to support the user's lower leg;
   mating a shock absorber insert with the base to provide shock absorption to the user's foot; and
   overmolding at least a portion of an outer sole to the base and the shock absorber insert.

2. The method of claim 1 wherein the base is provided within a mold, and wherein the overmolding of the outer sole comprises injecting a material into the mold and allowing the material to form to the base.

3. The method of claim 1 wherein the providing of the base further comprises injecting a first material into a mold to form the base, and wherein the overmolding of the outer sole comprises injecting a second material into the mold and allowing the second material to form to the base.

4. The method of claim 1 wherein the base is provided within a mold, and wherein the overmolding of the outer sole comprises injecting a material into the mold and allowing the material to form to the base with at least a portion of the outer sole being formed to the base and the shock absorber insert.

5. The method of claim 1 wherein the base comprises a section configured to support the user's posterior portion of the heel, the method further comprising overmolding a heel cushion to an interior portion of said section, wherein the outer sole and the heel cushion comprise a continuous material overmolded to the base using a single shot process.

6. The method of claim 5 wherein the base is provided within a mold, and wherein the overmolding of the outer sole and the heel cushion comprises injecting a material into the mold and allowing the material to form to the base.

7. The method of claim 1 wherein the base comprises a section configured to support the user's posterior portion of the heel, the method further comprising overmolding a heel bumper to the base with at least a portion of the heel bumper being arranged with an exterior portion of said section, wherein the outer sole and the heel bumper comprise a continuous material overmolded to the base using a single shot process.

8. The method of claim 7 wherein the base is provided within a mold, and wherein the overmolding of the outer sole and the heel bumper comprises injecting a material into the mold and allowing the material to form to the base.

9. The method of claim 1 wherein the base comprises a section configured to protect the forward end of the user's toes, the method further comprising overmolding a toe bumper to the section, wherein the outer sole and the toe bumper comprise a continuous material overmolded to the base using a single shot process.

10. The method of claim 9 wherein the base is provided within a mold, and wherein the overmolding of the outer sole and the toe bumper comprises injecting a material into the mold and allowing the material to form to the base.

11. A method of manufacturing an orthopedic walking boot, comprising:
   providing a base configured to support a user's foot and receive a support assembly configured to support the user's lower leg;
   mating a shock absorber insert with the base to provide shock absorption to the user's foot; and
   integrally forming at least a portion of an outer sole to the base and the shock absorber insert.

12. The method of claim 11 wherein the base is provided within a mold, and wherein the forming of the outer sole comprises injecting a material into the mold and allowing the material to form to the base.

13. The method of claim 11 wherein the providing of the base further comprises injecting a first material into a mold to form the base, and wherein the forming of the outer sole comprises injecting a second material into the mold and allowing the second material to form to the base.

14. The method of claim 11 wherein the base is provided within a mold, and wherein the forming of the outer sole comprises injecting a material into the mold and allowing the material to form to the base with at least a portion of the outer sole being formed to the base and the shock absorber insert.

15. The method of claim 11 wherein the base comprises a section configured to support the user's posterior portion of the heel, the method further comprising integrally forming a heel cushion to an interior portion of said section, wherein the outer sole and the heel cushion comprise a continuous material formed to the base using a single shot process.

16. The method of claim 15 wherein the base is provided within a mold, and wherein the forming of the outer sole and the heel cushion comprises injecting a material into the mold and allowing the material to form to the base.

17. The method of claim 11 wherein the base comprises a section configured to support the user's posterior portion of the heel, the method further comprising integrally forming a heel bumper to the base with at least a portion of the heel bumper being arranged with an exterior portion of said section, wherein the outer sole and the heel bumper comprise a continuous material overmolded to the base using a single shot process.

18. The method of claim 17 wherein the base is provided within a mold, and wherein the forming of the outer sole and the heel bumper comprises injecting a material into the mold and allowing the material to form to the base.

19. The method of claim 11 wherein the base comprises a section configured to protect the forward end of the user's toes, the method further comprising integrally forming a toe bumper to the section, wherein the outer sole and the toe bumper comprise a continuous material overmolded to the base using a single shot process.

20. The method of claim 19 wherein the base is provided within a mold, and wherein the forming of the outer sole and the toe bumper comprises injecting a material into the mold and allowing the material to form to the base.

21. A method of manufacturing an orthopedic walking boot, comprising:
providing a base configured to support a user's foot and receive a support assembly configured to support the user's lower leg, the base comprising a section configured to support the user's posterior portion of the heel;
mating a shock absorber insert with the base to provide shock absorption to the user's foot; and
overmolding an outer sole and at least one of a heel cushion and heel bumper to
the base and the shock absorber insert using a single shot process with said at least one of the heel cushion and heel bumper being arranged with the section.

22. A method of manufacturing an orthopedic walking boot, comprising:
providing a base configured to support a user's foot and receive a support assembly configured to support the user's lower leg, the base comprising a first section to protect the forward end of the user's toes and a second section to support the user's posterior portion of the heel;
mating a shock absorber insert with the base to provide shock absorption to the user's foot; and
overmolding an outer sole, a toe bumper, a heel cushion and a heel bumper to the base using a single shot process;
wherein at least a portion of the outer sole is overmolded to the base and the shock absorber insert, the toe bumper is overmolded to the first section, the heel cushion is overmolded to an interior portion of the second section, and the heel bumper is overmolded to the second section with at least a portion of the heel bumper arranged with an exterior portion of the second section.

* * * * *